United States Patent [19]

Elrod et al.

[11] Patent Number: 5,861,264
[45] Date of Patent: Jan. 19, 1999

[54] ANTI-TRYPTASE DETECTION AS A DIAGNOSTIC FOR INFLAMMATORY DISEASES

[75] Inventors: Kyle C. Elrod, Fremont; Richard D. Tanaka, Moraga, both of Calif.

[73] Assignee: Axys Pharmaceuticals, Inc., So. San Francisco, Calif.

[21] Appl. No.: 646,787

[22] Filed: May 21, 1996

[51] Int. Cl.⁶ ............................ G01N 33/53; C07K 16/00
[52] U.S. Cl. ................ 435/7.24; 530/387.1; 530/388.26; 530/389.2; 435/7.1; 435/7.92; 435/7.93; 435/7.95; 436/506
[58] Field of Search ........................... 435/7.1, 7.7, 7.29, 435/7.72, 7.9, 7.92, 7.93, 7.95; 530/387.1, 388.2, 388.26, 389.2; 436/506

[56] References Cited

U.S. PATENT DOCUMENTS 5,594,116  1/1997  Niles et al. .............................. 530/413

FOREIGN PATENT DOCUMENTS 0 379 295   7/1990   European Pat. Off. .
0 419 292   3/1991   European Pat. Off. .
WO 97/06440  2/1997   WIPO .

OTHER PUBLICATIONS

Fiebeger et al., J. Clin. Invest., vol. 96: 2606–2612, Dec. 1995.

Ausubel et al., Current Protocols in Molecular Biology, Green Pub. Assn. and Wiley Interscience. 1992, pp. 11.2.1–11.2.5, Dec. 1991.

Smith, Catherine H., et al., "Mast cell number and phenotype in chronic idiopathic urticaria", *J Allergy Clin Immunol*, vol. 96, No. 3, pp. 360–364 (Sep. 1995).

Lavery, J.P., "Preliminary study of the tyrptase levels in the synovial fluid of patients with inflammatory arthritis," *Division of Rheumatology, Department of Internal Medicine, The University of Texas Medical Branch, Galveston, Texas*, vol. 72, May 1994, pp. 425–427.

Halpern, G.M., "In vitro diagnosis in asthma: the state–of–the–art," *Allergie et Immunologie*, vol. 23, (1991) pp. 255–262.

*Primary Examiner*—Frank C. Eisenschenk
*Assistant Examiner*—Patrick J. Nolan
*Attorney, Agent, or Firm*—Townsend and Townsend and Crew LLP

[57] ABSTRACT

This invention provides methods of detecting mast cell mediated disease in an individual by detecting the presence in the individual of autoantibodies against mast cell specific proteins, such as tryptase and chymase. Specific mast cell mediated diseases detected by this invention include asthma, rheumatoid arthritis and SLE. The invention also provides a method of detecting autoantibodies against a mast cell specific protein. The method comprises exposing a sample to an sbp member complementary to the autoantibody and detecting the specific binding between the autoantibody and the sbp member. A related aspect of the invention provides methods of treating mast cell mediated diseases by monitoring for the presence of these autoantibodies. Another aspect of the invention relates to a composition comprising an autoantibody against a mast cell specific protein and the mast cell specific protein. A related aspect of the invention is to a method of forming a composition comprising an immune complex of a tryptase autoantibody and tryptase, wherein the complex is bound to a solid support.

35 Claims, 4 Drawing Sheets

Table I: Anti-Tryptase IgM Results

| Indication | Positive | Weak Positive | Negative | Totals | Frequency |
|---|---|---|---|---|---|
| SLE | 0 | 0 | 3 | 3 | 0% |
| RA | 3 | 1 | 1 | 5 | 80% |
| Severe Asthma | 6 | 2 | 16 | 24 | 33% |
| Normal | 3 | 2 | 27 | 32 | 16% |

Table II: Anti-Tryptase IgG Results

| Indication | Positive | Weak Positive | Negative | Totals | Frequency |
|---|---|---|---|---|---|
| SLE | 1 | 1 | 1 | 3 | 67% |
| RA | 2 | 1 | 2 | 5 | 60% |
| Severe Asthma | 7 | 0 | 17 | 24 | 29% |
| "Normal" | 2 | 0 | 30 | 32 | 6% |

Table III: Combined Anti-Tryptase IgG and IgM Results
(Either IgG or IgM positive)

| Indication | Positive | Weak Positive | Negative | Totals | Frequency |
|---|---|---|---|---|---|
| SLE | 1 | 1 | 1 | 3 | 67% |
| RA | 4 | 1 | 0 | 5 | 100% |
| Severe Asthma | 12 | 2 | 10 | 24 | 58% |
| Disease Total | 17 | 4 | 11 | 32 | 66% |
| "Normal" | 5 | 2 | 25 | 32 | 22% |

FIG. 2

Table IV: Sample Result Calls

| Wall's Samples (Name) | Anti-Tryptase Results | | Indication |
|---|---|---|---|
| | IgG | IgM | |
| TB003 | POS | NEG | SA |
| PGCG4 | POS | NEG | SA |
| MS19 | POS | NEG | SA |
| LC40 | POS | NEG | SA |
| CHI33 | POS | NEG | SA |
| CHI31 | POS | NEG | SA |
| ESI12 | POS | POS | SA |
| ES29 | NEG | POS | SA |
| GBI005 | NEG | POS | SA |
| HBCG2 | NEG | POS | SA |
| PL17 | NEG | POS | SA |
| TBI13 | NEG | POS | SA |
| LWCG3 | NEG | WKPOS | SA |
| SJ009 | NEG | WKPOS | SA |
| AHI15 | NEG | NEG | SA |
| AM004 | NEG | NEG | SA |
| CG5 | NEG | NEG | SA |
| JCL14 | NEG | NEG | SA |
| JNI006 | NEG | NEG | SA |
| KPI18 | NEG | NEG | SA |
| LHI007 | NEG | NEG | SA |
| NHI30 | NEG | NEG | SA |
| SW37 | NEG | NEG | SA |
| SWI16 | NEG | NEG | SA |

FIG. 3A

| Seriologics | IgG | IgM | Indication |
|---|---|---|---|
| 07747-FT0507238 | POS | POS | RA |
| 11035X | POS | NEG | RA |
| 08257A | POS | NEG | SLE |
| 679A-FT05060891 | WKPOS | POS | RA |
| 11168X | WKPOS | NEG | SLE |
| 07747-FT05057238 | NEG | POS | RA |
| 679A-FT05060455 | NEG | WKPOS | RA |
| 32121B | NEG | NEG | SLE |

| Normal Donors | IgG | IgM | Indication |
|---|---|---|---|
| 334 | POS | NEG | Normal |
| 326 | POS | NEG | Normal |
| 377 | NEG | POS | Normal |
| 364 | NEG | POS | Normal |
| 351 | NEG | POS | Normal |
| 375 | NEG | WKPOS | Normal |
| 372 | NEG | WKPOS | Normal |
| 374 | NEG | NEG | Normal |
| 373 | NEG | NEG | Normal |
| 368 | NEG | NEG | Normal |
| 366 | NEG | NEG | Normal |
| 365 | NEG | NEG | Normal |
| 359 | NEG | NEG | Normal |
| 358 | NEG | NEG | Normal |
| 354 | NEG | NEG | Normal |
| 353 | NEG | NEG | Normal |
| 352 | NEG | NEG | Normal |
| 345 | NEG | NEG | Normal |
| 338 | NEG | NEG | Normal |
| 336 | NEG | NEG | Normal |
| 335 | NEG | NEG | Normal |
| 333 | NEG | NEG | Normal |
| 331 | NEG | NEG | Normal |
| 330 | NEG | NEG | Normal |
| 328 | NEG | NEG | Normal |
| 327 | NEG | NEG | Normal |
| 325 | NEG | NEG | Normal |
| 323 | NEG | NEG | Normal |
| 314 | NEG | NEG | Normal |
| 309 | NEG | NEG | Normal |
| 308 | NEG | NEG | Normal |
| 306 | NEG | NEG | Normal |

FIG. 3B

ANTI-TRYPTASE DETECTION AS A DIAGNOSTIC FOR INFLAMMATORY DISEASES

BACKGROUND OF THE INVENTION

1. Field of the Invention

This invention relates to methods for the detection and monitoring of mast-cell mediated inflammatory disease states. The invention includes methods for the detection and monitoring of inflammatory diseases associated with the respiratory tract, such as asthma.

2. Background of the Invention

Inflammation, both acute and chronic, is a major contributor to a wide variety of mammalian disease states. Several diseases, such as asthma, have now been linked to the presence of an inflammation-related condition.

One initiator of the inflammatory sequence is an allergic response to inhaled allergens. Leukocytes carrying IgE receptors, notably mast cells and basophils, but also including monocytes, macrophages, and eosinophils, are present in the epithelium and underlying smooth muscle tissues of bronchi where they are activated initially by binding of specific inhaled antigens to the IgE receptors. Activated mast cells release a number of preformed or primary chemical mediators of the inflammatory response and enzymes. In addition, several large molecules are released by degranulation of mast cells: proteoglycans, peroxidase, arylsulfatase B, and notably the proteases tryptase and chymotryptic proteinase (chymase). See, DRUG THERAPY OF ASTHMA, pp. 1054–54.

This chemical release from mast cells probably accounts for the early asthmatic response that occurs in susceptible individuals after exposure to airborne allergens. The late asthmatic reaction is accompanied by a marked increase in the number of inflammatory cells infiltrating bronchiolar smooth muscle and epithelial tissues, and spilling into the airways. These cells include eosinophils, neutrophils, and lymphocytes, all of which are attracted to the site by release of mast cell derived chemotactic agents.

Tryptase is the major secretory protease of human mast cells and is proposed to be involved in neuropeptide processing and tissue inflammation. Mature human tryptase is a glycosylated, heparin-associated tetramer of heterogenous, catalytically active subunits. See, e.g., Vanderslice et al. *Proc. Natl. Acad. Sci. USA* 87:3811–3815 (1990); Miller et al., *J. Clin. Invest.* 86:864–870 (1990); Miller et al. *J. Clin. Invest.* 84:1188–1195 (1989); and Vanderslice et al. *Biochemistry* 28:4148–4155 (1989).

Tryptase is stored in mast cell secretory granules. After mast cell activation, human tryptase can be measured readily in a variety of biologic fluids. For example, after anaphylaxis, tryptase appears in the bloodstream, where it remains detectable for several hours. See, Schwartz et al., *N. Engl. J. Med.* 316:1622–1626 (1987). Its appearance has been detected in samples of nasal and lung lavage fluid from atopic subjects challenged with specific antigen. See, Castells and Schwartz, *J. Allerg. Clin. Immunol.* 82:348–355 (1988) and Wenzel, et al., *Am. Rev. Resp. Dis.* 141:563–568 (1988). Tryptase levels in lung lavage fluid obtained from atopic asthmatics increase after endobronchial allergen challenge.

Anti-tryptase antibodies have been prepared by injecting tryptase from rats into rabbits and isolating the polyclonal rabbit anti-tryptase IgG fraction. The ability of this IgG fraction to inhibit HIV infection and syncytia formation was tested ("Anti-tryptase antibody and composition for treatment of AIDS using the same", Katunama et al., EP 0 379 295). The same investigators reported a human tryptase-like protein isolated from human lymphoblastic leukemia cells ("Human tryptase-like protein", Katunama et al., EP 0 419 292) and prepared polyclonal rabbit antisera against this human tryptase-like protein.

Several diseases have been traced to an immune response mounted by the body against its own normal, endogenous body constituents. These diseases are generally termed autoimmune diseases and include systemic lupus erythematosus (SLE), insulin dependent diabetes and Addison's disease. Frequently, an autoimmune disease is characterized by the presence of autoantibodies against a specific normal, endogenous body constituent(s). For example, multiple sclerosis has been associated with the presence of autoantibodies against myelin basic protein; peripheral neuropathies with the presence of autoantibodies against nervous system glycolipids and glycoproteins (GA1, GM2 and GM2 and MAG) and systemic lupus erythematosus with the presence of autoantibodies against the Sm antigen.

Mast cell mediated inflammatory conditions are a growing public health concern. In particular, asthma has become a common chronic disease in industrialized countries. Therefore, it would be desirable to provide improved methods of detecting such inflammatory disease, both to select an appropriate therapy and to monitor the effectiveness of a chosen therapeutic regimen. In addition, it would be desirable to have prognostic tools to detect the onset of inflammation before progression of the disease to the symptomatic state. This invention fulfills this and related needs, partly by detecting the presence of autoantibodies against mast cell specific proteins.

SUMMARY OF THE INVENTION

This invention provides methods of detecting a mast cell mediated disease in an individual by detecting the presence in the individual of autoantibodies against mast cell specific proteins, such as tryptase and chymase. Specific mast cell mediated diseases detected by this invention include asthma, rheumatoid arthritis(RA) and SLE. Detection of the autoantibodies is usually done by an immunoassay, with the enzyme-linked immunosorbent assay being a preferred method of detection. The mast cell protein, or an analog thereof is immobilized on a solid support and exposed to a sample from the patient. Binding of autoantibodies in the sample to the immobilized protein is detected and correlated to the presence of the disease.

The invention also provides a method of detecting autoantibodies against a mast cell specific protein, said method comprising exposing a sample to an sbp member complementary to the autoantibody and detecting the specific binding between the autoantibody and the sbp member.

Another aspect of the invention relates to a composition comprising an autoantibody against a mast cell specific protein and the mast cell specific protein. A related aspect of the invention is to a method of forming a composition comprising an immune complex of a tryptase autoantibody and tryptase, wherein said complex is bound to a solid support.

DETAILED DESCRIPTION OF THE INVENTION

This invention provides methods of detecting mast cell mediated diseases in a patient by detecting the presence in a sample from the patient of autoantibodies against mast cell specific proteins. It has been discovered that in a variety of mast cell mediated diseases, such diseases being those characterized by mast cell degranulation and leakage of mast cell specific proteins into other tissue, autoantibodies are produced against these mast cell specific proteins and that the titer of these autoantibodies is an indication of a disease state. Thus, the present invention provides methods of diagnosing mast cell mediated diseases based on the detection of the presence of autoantibodies against mast cell specific proteins.

The term "mast cell mediated disease" refers to a disease state which results in the activation and degranulation of mast cells and release of their contents such that the contents are present in the extracellular space at levels elevated above normal.

The term "mast cell specific protein" refers to proteins which are released by mast cells upon degranulation and are not otherwise predominantly found in or released by other cells in the body. A protein that is "predominantly released from mast cells" means that when the protein is present at levels elevated above normal, greater than 95% of the amount by which it is elevated above normal is a result of release of the protein from degranulated mast cells, i.e., the source of greater than 95% of the mast cell specific protein above the normal level is degranulated mast cells. Preferably, this amount is greater than 99%, and more preferably greater than 99.5%. Examples of mast cell specific proteins include, but are not limited to, tryptase, chymase, human mast cell-carboxypeptidase (HMC-CP) and related mast cell proteases, *Asthma and Rhinitis,* W. W. Busse and S. T. Holgate (eds.) pages 168, 201, 806 (1995) (Blackwell, oxford); G. M. Goldstein et al., "Human Mast Cell Carboxypeptidase: Purification and Characterization" *J. Clin. Investigation,* 83, 1630–1636 (1989) and L. B. Schwartz, "Mast Cells: function and contents", *Curr. Opin. Immunol.,* 6(1), 91–97 (1994).

The term "autoantibodies", refers to antibodies produced by a patient against a substance endogenous or native to the patient. Thus, unlike antibodies, which are produced by the immune system against foreign proteins, autoantibodies are produced against native constituents, i.e., the immune system is attacking self proteins.

"Sample" shall mean any sample that is reasonably suspected of containing an autoantibody. Such samples can include human, animal or man-made samples. The sample can be prepared in any convenient medium which does not interfere with the assay. Typically, the sample is an aqueous solution or biological fluid as described in more detail below.

The sample may be a biological fluid such as, but not limited to, whole blood, serum, plasma, nasal secretions, sputum, urine, sweat, saliva, tear fluid, faeces, transdermal exudates, pharyngeal exudates, bronchoalveolar lavage, tracheal aspirations, cerebrospinal fluid, or the like. Serum and plasma are preferred because of their high antibody titer.

"Specific binding pair member" (sbp member) shall mean a molecule which is one of two different molecules, having an area on the surface or in a cavity which specifically binds to and is thereby defined as being complementary with a particular spatial and polar organization of the other molecule. The two molecules are related in the sense that their binding to each other is such that they are capable of distinguishing their binding partner from other assay constituents having similar characteristics. The members of the specific binding pair are referred to as ligand and receptor (antiligand), sbp member and sbp partner, and the like. Complementary sbp members bind to each other, as for example, a ligand and its complementary receptor. Sbp members will usually be members of an immunological binding pair such as an antigen-antibody, although other specific binding pairs, such as biotin-avidin, hormones-hormone receptors, nucleic acid duplexes, IgG-protein A, and the like are specific binding pairs which are not immunological binding pairs. Specific immunological binding pairs include mast cell specific proteins and autoantibodies against them, e.g., tryptase and anti-tryptase autoantibody.

"Antigen" shall mean any compound capable of binding to an antibody, or against which antibodies can be raised.

"Antibody" shall mean an immunoglobulin having an area on its surface or in a cavity that specifically binds to and is thereby defined as complementary with a particular spatial and polar organization of another molecule. The antibody can be polyclonal or monoclonal. Antibodies may include a complete immunoglobulin or fragments thereof, which immunoglobulins include the various classes and isotypes, such as IgA (IgA1 and IgA2), IgD, IgE, IgM, and IgG (IgG1, IgG2, IgG3, and IgG4) etc. Fragments thereof may include Fab, Fv and F(ab')$_2$, Fab', and the like.

The term "mast cell specific protein analog" refers to a modified mast cell specific protein or surrogate that can compete with the mast cell specific protein for binding to an sbp member complementary to the analyte or ligand, such as an autoantibody against the mast cell specific protein. Thus, they both bind to the autoantibody in a manner similar to the mast cell specific protein. The surrogate could be, for example, an antibody directed against the idiotype of an autoantibody to mast cell specific protein.

The term "specific binding" between two molecules refers to their binding to each other such that they are capable of distinguishing their binding partner from other assay constituents having similar characteristics. Typically, specific binding exists when the dissociation constant for a dimeric complex is $\leq 1$ $\mu$M, preferably $\leq 100$ nM and most preferably $\leq 1$ nM.

The term "effective amount" refers to the amount required to produce the desired effect. Thus, the therapeutically effective amount of a drug is the amount required to treat, alleviate or ameliorate the disease for which the drug is being administered.

It should be recognized that this invention includes, not merely the detection of autoantibodies to mast cell specific proteins disclosed herein, but the detection of disease states by correlating the presence of such autoantibodies to presence of a disease state. This correlation is independent of the detection method employed and as such, several methods may be used to detect the presence of autoantibodies to mast cell specific proteins and thus detect the presence of disease. These methods will generally detect the binding of the autoantibody to a ligand which is a specific binding pair member complementary to the autoantibody. Methods which employ or detect the binding of an antibody to its complementary sbp member (e.g., its antigen) are numerous and are grouped by those of skill in the art under the broad categorization of immunoassays. Therefore, it will be apparent that many different immunoassay methodologies can be used in practicing this invention.

The diagnostic methods of the present invention require techniques for detecting specific interaction between autoantibodies to mast cell specific proteins (e.g., tryptase) and sbp members (ligands) complementary to such autoantibodies. The particular assay protocol chosen is not critical, and it is necessary only that the assay be sufficiently sensitive to detect a threshold level of the autoantibody which is considered to be positive. Since normal, i.e., individuals not having a mast cell mediated disease do not have such autoantibodies, the threshold level is any level above zero. In the assay, this corresponds to a level of signal that is over the background signal observed with normal negative control samples. In order to minimize the occurrence of false positive results, this threshold level is typically set at about two standard deviations above the background signal, more typically about three standard deviations above the background signal and most preferably about four standard deviations above the background signal.

Suitable assays include both solid phase (heterogeneous) and non-solid phase (homogeneous) protocols. The assays can be run using competitive or non-competitive formats, and using a wide variety of labels, such as radioisotopes, enzymes, fluorescers, chemiluminescers, spin labels, and the like.

Such methods include, but are not limited to enzyme-linked immunosorbent assays (ELISA), both direct and reverse formats, and other solid phase assays such as Immunoconcentration™ assays, radial partition immunoassay and dot-blot screening, radioimmunoassay, immunofluorescence, indirect immunofluorescence, fluorescence energy transfer (FETIA™), particle counting assays (PACIA™), particle-enhanced turbidimetric inhibition (PETINIA™), nephelometry, capillary immunoelectrophoresis, rocket electrophoresis, agglutination immunoassays, homogenous immunoassays, such as EMIT™, enzyme membrane immunoassay (EMIA™), luminescent oxygen channelling immunoassay (LOCI) (Ullman, E. F., et al., Proc. Natl. Acad. Sci., 91, 5426–5430 (1994), enzyme channelling and fluorescence protection (FPIA™), and the like. See, Gosling, Clin. Chem., 36(8): 1408–1427 (1990) and Miyai, Adv. in Clin. Chem., 24:62–110 (1985). Representative examples where some of these assays been used to detect autoantibodies are described in U.S. Pat. Nos. 4,487,830; 5,200,318; 5,405,749; 5,407,802 and 5,443,952. Occasionally, initial purification steps, such as separating the antibody fraction by precipitation or chromatography may be performed prior to probing the purified fraction for the presence of the autoantibody.

Some assays rely on heterogeneous protocols where a ligand complementary to the autoantibody is bound to a solid phase which is used to separate the ligand-autoantibody complex that forms when autoantibody is present in a serum sample. The ligand may be conveniently immobilized on a variety of solid phases, such as dipsticks, particulates, microspheres, magnetic particles, test tubes, microtiter wells, and nitrocellulose or nylon membranes and the like.

The solid phase is exposed to a patient sample so that the autoantibody, if any, is captured by the ligand. By then removing the solid phase from the patient sample, the captured autoantibody is removed from unbound autoantibodies and other contaminants in the sample. The captured autoantibody can then be detected using the non-competitive "sandwich" technique where a labelled second ligand for the autoantibody is exposed to the washed solid phase. Alternatively, competitive formats rely on the prior introduction of a labelled antiligand antibody to the serum sample so that labelled antiligand and autoantibody compete for binding to the solid phase ligand. Such assay techniques are well known and well described in both the patent and scientific literature. See, e.g., U.S. Pat. Nos. 3,791,932; 3,817,837; 3,839,153; 3,850,752; 3,850,578; 3,853,987; 3,867,517; 3,879,262; 3,901,654; 3,935,074; 3,984,533; 3,996,345; 4,034,074; and 4,098,876. Enzyme-linked immunosorbent assay (ELISA) methods are described in detail in U.S. Pat. Nos. 3,791,932; 3,839,153; 3,850,752; 3,879,262; and 4,034,074. ELISA assays detect very low titers of autoantibodies.

Autoantibodies can also be detected by solid-phase radioimmunoassay (RIA). The solid phase is exposed to the sample in the presence of radiolabelled antibodies that compete for binding to the immobilized ligand. In this assay, the amount of radiolabel bound to the solid phase is inversely related to the amount of autoantibodies initially present in the sample. After separation of the solid phase, nonspecifically bound radiolabel is removed by washing, and the amount of radiolabel bound to the solid phase determined. The amount of bound radiolabel is, in turn, related to the amount of autoantibodies initially present in the sample.

A commonly used assay format is the antibody capture assay. The general protocol is simple: a ligand, i.e., an unlabelled specific binding member for the autoantibody is immobilized on a solid phase, and the autoantibody is allowed to bind to the immobilized spb member. The autoantibody can be labelled directly or can be detected by using a labelled secondary reagent that will specifically recognize the autoantibody. The strength of signal from the bound label allows the determination of the amount of autoantibody present in the sample.

The immobilized sbp member will frequently be the mast cell specific protein, or an analog thereof, to which the autoantibody specifically binds. Analogs of the mast cell specific protein include epitopic fragments recognized by the autoantibody and anti-idiotypic antibodies to the mast cell specific protein. For example, when autoantibodies to tryptase are being detected, tryptase or a fragment thereof, or an anti-idiotypic antibody to tryptase can be bound to the support.

Fragments of tryptase may be synthetic peptides corresponding to specific amino acid sequences of the tryptase molecule prepared de novo or fragments may be obtained by chemical or enzymatic cleavage (e.g., by proteolysis) of naturally occurring tryptase. Synthetic proteins and polypeptides can be synthesized by the well known Merrifield solid-phase synthesis method in which amino acids are sequentially added to a growing chain. See Merrifield (1963), J. Am. Chem. Soc. 85:2149–2156. Automatic peptide synthesizers are commercially available from numerous suppliers, such as Applied Biosystems, Foster City, Calif.

A variant of this method is the immunoprecipitation technique. In this method, a labelled mast cell specific protein is allowed to bind to the autoantibody and the immunocomplexes are precipitated with polyethylene glycol, or Staphylococcus A, protein A or protein G immobilized on beads or other solid support. After several washings, the immunoprecipitates are analyzed for the presence of label. Optionally, an unlabelled mast cell specific protein can be added to compete with the labelled protein for binding to the autoantibody.

When antibody capture assays are done with excess antigen (e.g., tryptase) on the solid phase, enough to saturate all the available autoantibody, both the presence and level of autoantibody in a sample can be measured and compared to that in other samples. A test sample suspected of containing the autoantibody is allowed to bind to the antigen on the solid phase and that binding is detected as described earlier. To quantitate and compare the levels of autoantibody in the samples, a titration of the test samples is done by serial dilution, thus yielding the relative titers of the autoantibodies in the samples.

A variety of labelled secondary reagents can be used to detect the presence of the bound autoantibody. Examples include anti-immunoglobulin antibodies, protein A and protein G. Since one is typically screening samples from human patients, greater specificity usually results from using anti-human immunoglobulin antibodies.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), calorimetric labels such as colloidal gold or colored glass or plastic (e.g., polystyrene, polypropylene, latex, etc.) beads and chemiluminscent labels. Patents teaching the use of such labels include U.S. Pat. Nos. 3,817,837; 3,850,752; 3,939,350; 3,996,345; 4,277,437; 4,275,149; and 4,366,241.

Means of detecting such labels are well known to those of skill in the art. Thus, for example, radiolabels may be detected using photographic film or scintillation counters, fluorescent or chemiluminescent markers may be detected using a photodetector to detect emitted light. Enzymatic labels are typically detected by providing the enzyme with a substrate and detecting the reaction product produced by the action of the enzyme on the substrate, and colorimetric labels are detected by simply visualizing the colored label.

Other formats can first separate the entire antibody fraction (e.g., by binding to a solid support). This fraction can subsequently be probed with labelled mast cell specific protein for the presence of specific antibody to the mast cell specific protein. As the above discussion indicates, a wide variety of methodologies for detection of antibodies are available and all such methods for detection of autoantibodies to tryptase or other mast cell specific proteins can be used in practicing this invention.

Disease states detected by determining the presence of autoantibodies to mast cell specific proteins generally include those diseases in which mast cell degranulation and release of such proteins occurs. Typically, these proteins are released into the interstitial spaces surrounding the mast cells and the bloodstream. Since mast cell degranulation is associated with the allergic response and inflammatory disease, such disease states are particularly amenable to detection by the methods disclosed herein. Specific examples include, but are not limited to, rheumatoid arthritis, asthma (either early onset or chronic), systemic lupus erythematosus (SLE), psoriasis, scleroderma, rhinitis, keratoconjunctivitis, multiple sclerosis, interstitial cystitis, Krohn's disease, fibrosing alveolitis, bolus mastocytosis, urticara, chronic liver disease and inflammatory bowel disease, see, Rozniecki J. J. et al., *Ann. Neurol.,* 37, 63–66. (1995) and Farrell D. J. et al., *Hepatology,* 22, 1175–1181 (1995).

"Normal" individuals, i.e., those not exhibiting a mast cell mediated disease state do not have autoantibodies against tryptase or other mast cell specific proteins. Samples from normal individuals can be used, if necessary to establish a baseline or control level of signal in the particular assay used. Thus, a patient sample showing a level of signal above this baseline level indicates the presence of a mast cell mediated disease such as asthma, rheumatoid arthritis or SLE.

In addition to detecting the presence of a mast cell mediated disease state, the detection of autoantibodies as described here is also of utility in monitoring the effectiveness of a particular therapeutic regimen against the disease. Levels of the autoantibody can be monitored and decreasing (or unchanged or increasing) levels over time can be used as an objective indication of whether the disease is being ameliorated (or not). Then, depending on the results of the assay, the dosage regimen can be adjusted accordingly, thus providing an improvement in the methods by which these diseases are treated. For example, drugs which can be monitored during treatment of asthma and other allergic or inflammatory conditions include, $Ca^{2+}$antagonists (e.g., verapamil, gallopamil), Leukotriene antagonists (e.g., picumast), β-adrenergics (e.g., formoterol), anticholinergics (e.g., atropine), glucocorticosteroids (e.g., budenoside, methylprednisone, beclamethasone), antiallergics (e.g., sodium cromoglycate, nedocromil sodium, theophylline) and cyclooxygenase inhibitors (indomethacin). Such screening methods can also be useful for the early diagnosis and treatment of otherwise asymptomatic patients.

The detection of autoantibodies against mast cell specific proteins such as tryptase and chymase and detection of the complexes between the autoantibodies and the mast cell specific proteins are also useful in developing and validating the assays described above. Detecting the presence of such binding and the presence of the immune complexes formed as a result of such binding in known positive controls or their absence in negative controls (i.e., normal patients) provides confidence in the accuracy of the assay and is typically necessary to obtain customer acceptance of the assay. Frequently, the immune complexes are isolated by binding them to a solid support and thereby separating them from the sample. The immune complexes are useful for developing standards for the assay. Generally, these methods comprise exposing a patient sample to an sbp member complementary to an autoantibody against a mast cell specific protein and detecting the specific binding between the sbp member and the autoantibody in accordance with the methods described above. As described above, the mast cell specific protein is preferably tryptase and the sbp member is tryptase or an analogous ligand which is capable of competing with tryptase for binding to autoantibodies against tryptase. The preceding discussion of assay methodologies, labels, solid supports etc., is also equally applicable.

EXAMPLE

Detection of Tryptase Autoantibodies and Correlation to Disease

Materials and Methods:

Samples and reagents: Serum and plasma samples from patients with severe asthma (SA), systemic lupus erythematosus (SLE), rheumatoid arthritis (RA) as well as plasma and serum from normal donors (individuals without HIV, HBV or HCV markers) were obtained from Serologics and the laboratory of Andrew Walls. Human lung tryptase was obtained from Dr. Jim Travis. ELISA reagents, substrate, and antibody conjugates are products of the Sigma Chemical Company.

Figure 1A:
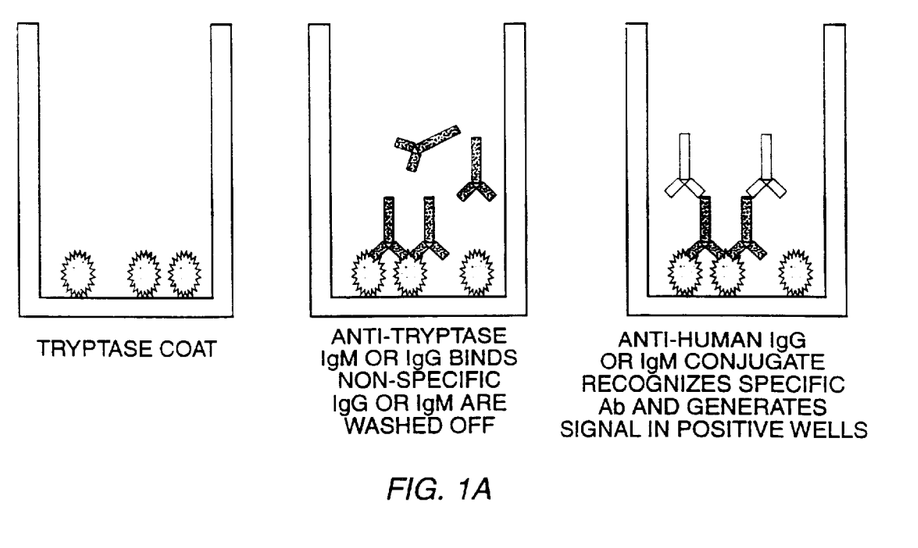
FIG. 1A shows a direct ELISA format for an anti-tryptase diagnostic.
Figure 1B:
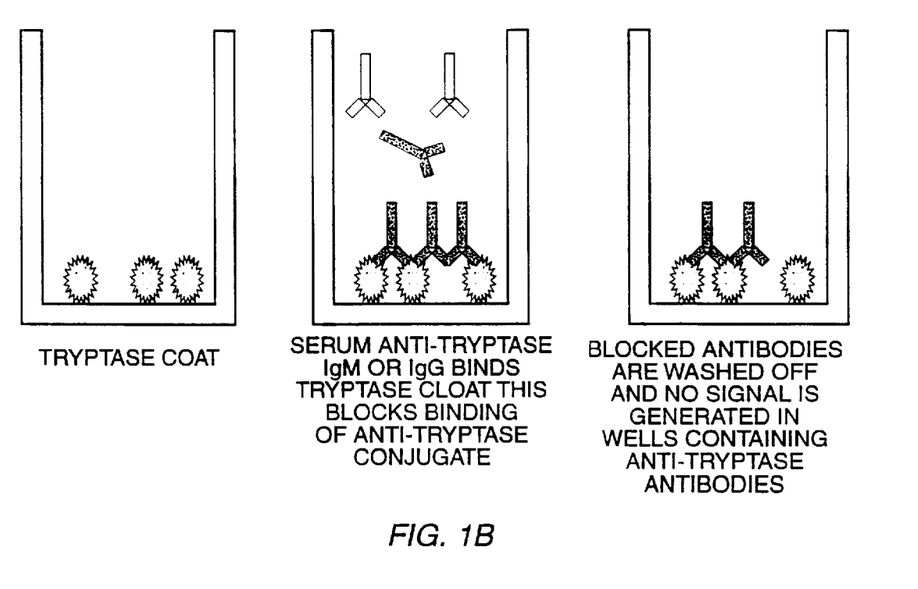
FIG. 1B shows a competitive ELISA format for an anti-tryptase diagnostic.

ELISA: An enzyme linked immunosorbant assay (ELISA) using direct detection of anti-tryptase antibodies (IgG or IgM, FIG. 1A) was developed. Microtiter plate wells (Nunc Maxisorb™) were coated with human lung tryptase (5 μg/mL, 100 μL per well) in 0.1M sodium carbonate, pH 9.6. Plates were incubated overnight at 4° C. Wells were washed four times with 300 μL wash buffer (PBS (136.9 mM NaCl, 2.68 mM KCl, 10.14 mM $NaH_2PO_4$, 1.76 mM $KH_2PO_4$, pH 7.4) with added detergent (0.05% Tween-20)) on a plate washer (SLT Lab instruments). Nonspecific binding was blocked by adding 100 μL of 1% BSA in PBS to each well and incubating for one hour at room temperature. The plates were washed. Samples diluted in PBS (1:10) were added to wells (100 μL per well), allowed to bind for one hour at 37° C., and the plates were washed. Alkaline phosphatase conjugate of either goat-anti-human IgG (1:20,000 in PBS, 100 μL) or goat-anti-human IgM (1:30,000 in PBS, 100 μL) was added to each well and incubated for one hour at 37° C., followed by washing. Substrate (para-nitrophenol phosphate, 1 mg/mL in 0.1M Tris pH 9.0, 100 μL) was added to each well and plates were incubated for 45 minutes at room temperature. The plate was read at 405 nm with background subtraction at 570 or 490 nm. Disease samples were assayed in duplicate and "normal" samples were assayed as single points.

Calculations: Commercial diagnostics use cutoff algorithms defined after extensive clinical trials. In general, cutoff algorithms should provide for separation between negative and positive samples (sensitivity) while reducing false positives (specificity). In our sample set, there were no true "negatives" to assist in cutoff calculation, only "normal" samples that tested negative for common infectious disease markers.

The following calculations were performed on absorbance values (AU) to assign anti-tryptase response. The mean and standard deviation of the "normal" samples were calculated. Any "normal" sample with AU>mean+2× standard deviation was defined as positive and excluded from the "normal" set. If necessary, new mean and standard deviation were calculated, and disease sample responses were defined according to the following criteria:

POS=AU>"Normal" Mean+2×"Normal" Standard Deviation

WKPOS=AU>"Normal" Mean+1.5×"Normal" Standard Deviation

NEG=AU<"Normal" Mean+1.5×"Normal" Standard Deviation

Results:

A total of 32 disease and 32 "normal" serum and plasma samples were assayed. The response for each individual sample is summarized in Table IV. Tabulation of the results (Tables I–III) demonstrate that there is a higher frequency of positive specimens in the patient populations (21/32) than that of the "normal" (7/32) population. Distinct contrast is evident when comparing rheumatoid arthritis positive incidence (100%) to that of the "normal" population (22%).

Figure 2:
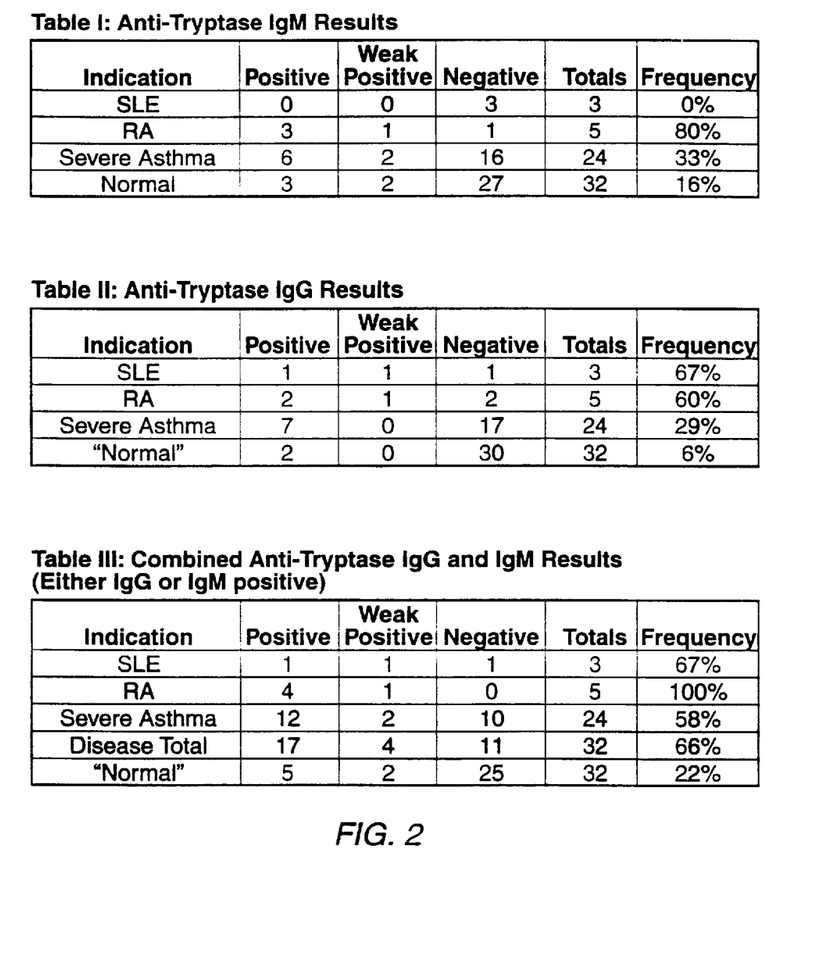
FIG. 2 shows the tabulation of combined results from screening normal patients and patients with SLE, RA and asthma.
Figure 3A:
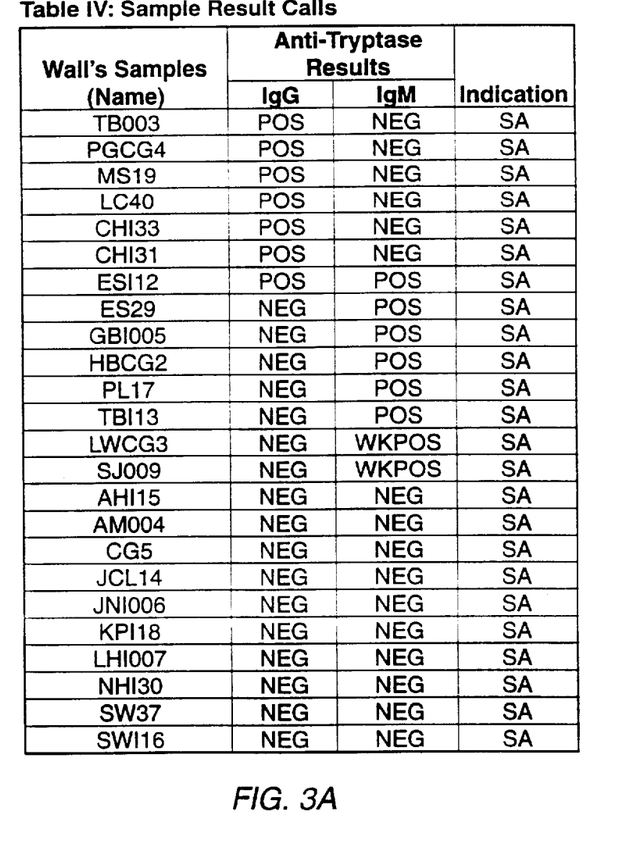
FIGS. 3A and 3B show the individual results from both normal patients and diseased patients.
Figure 3B:
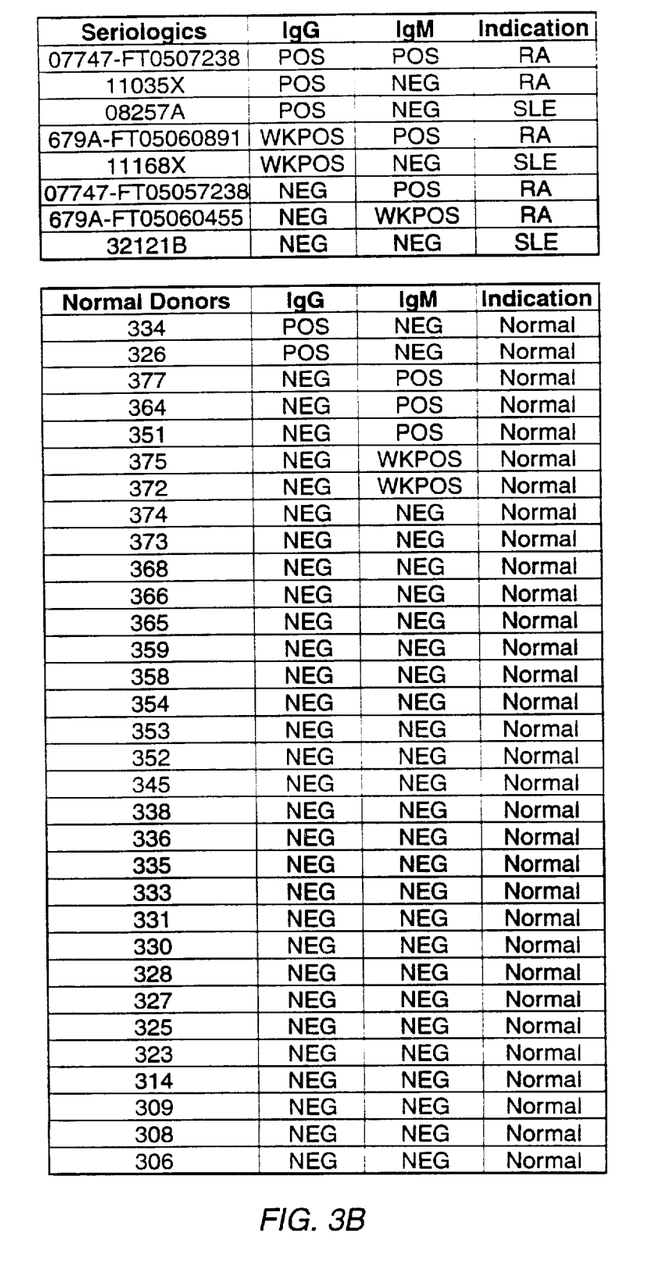

Conclusion:

The assays presented here detect the presence of tryptase autoantibodies and correlate their presence with disease states. The assay principle can apply to different detection systems. The assay format used was direct ELISA. Equally valid methods include the competitive ELISA format (FIG. 2), or immunoblotting formats using membrane surfaces rather than a microtiter plate to absorb the antibodies.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A method of detecting a mast cell mediated disease state in an individual, said method comprising:
   a) determining the presence of an autoantibody which binds to tryptase in a biological sample from the individual; and
   b) relating the presence of said autoantibody to the presence of the mast cell mediated disease state.

2. The method of claim 1, wherein the biological sample is serum or plasma.

3. The method of claim 1, wherein the disease state is an inflammatory disease.

4. The method of claim 3, wherein the disease state is rheumatoid arthritis, asthma or systemic lupus erythematosus.

5. The method of claim 4, wherein the disease is chronic asthma.

6. The method of claim 1, wherein said determining step (a) comprises:
   (i) providing a specific binding pair member (sbp member) complementary to the autoantibody;
   (ii) contacting the sbp member with the biological sample; and
   (iii) detecting binding between the sbp member and said autoantibody.

7. The method of claim 6, wherein the sbp member is tryptase or an antibody directed against the idiotype of an autoantibody to mast cell tryptase.

8. The method of claim 7, wherein the disease state is an inflammatory disease.

9. The method of claim 8, wherein the disease state is rheumatoid arthritis, asthma or systemic lupus erythematosus.

10. The method of claim 9, wherein the disease is chronic asthma.

11. The method of claim 6, said method being an enzyme linked immunosorbent assay (ELISA).

12. The method of claim 11, wherein said ELISA assay is a direct ELISA.

13. The method of claim 11, wherein said ELISA assay is a competitive ELISA.

14. The method of claim 6, further comprising a step of separating a complex formed between the sbp member and the autoantibody before the detecting step (iii).

15. The method of claim 6, wherein the sbp member complementary to the autoantibody is immobilized on a solid support and said contacting step (ii) comprises exposing the solid support to the biological sample, whereby the autoantibody in the biological sample binds to the sbp member to form a solid support with a bound autoantibody.

16. The method of claim 15, wherein the detecting step (iii) comprises:
   (1) exposing the solid support with bound autoantibody to a specific binding reagent for the autoantibody, said binding reagent being linked to a label, whereby the binding reagent binds to autoantibody bound to the sbp member on the support; and
   (2) detecting the presence of the label bound to the support, wherein the amount of label bound to the support is correlated to the presence of the autoantibody.

17. The method of claim 16, wherein the binding reagent is an antihuman antibody.

18. The method of claim 17, wherein the label is an enzyme.

19. The method of claim 18, wherein the enzyme is horseradish peroxidase, alkaline phosphatase or β-galactosidase.

20. The method of claim 15, wherein the contacting step (ii) further comprises exposing the support to a ligand complementary to the sbp member, said ligand being linked to a label, whereby said autoantibody and ligand compete for binding to the sbp member on the support, and the detecting step (iii) comprises detecting the label bound to the support, wherein the amount of label bound to the support is correlated to the presence of the autoantibody.

21. The method of claim 20, wherein the label is an enzyme.

22. The method of claim 21, wherein the enzyme is horseradish peroxidase, alkaline phosphatase or β-galactosidase.

23. A method of detecting an autoantibody which binds to tryptase in a sample, said method comprising:
   (a) contacting the sample with an sbp member complementary to the autoantibody: and
   (b) determining the specific binding between the autoantibody and the sbp member to detect the autoantibody.

24. The method of claim 23, wherein the sbp member is tryptase.

25. The method of claim 23, wherein the sbp member complementary to the autoantibody is immobilized on a solid support, and said contacting step (a) comprises exposing the solid support to the sample, whereby the autoantibody in the sample binds to the sbp member to form a solid support with a bound autoantibody.

26. The method of claim 25, wherein the determining step (b) comprises:
   (1) exposing the solid support with bound autoantibody to a specific binding reagent for the autoantibody, said binding reagent being linked to a label, whereby the binding reagent binds to autoantibody bound to the sbp member on the support; and
   (2) detecting the presence of the label bound to the support, wherein the amount of label bound to the support is correlated to the presence of the autoantibody.

27. The method of claim 26, wherein the binding reagent is an antihuman antibody.

28. The method of claim 27, wherein the label is an enzyme.

29. The method of claim 28, wherein the enzyme is horseradish peroxidase, alkaline phosphatase or β-galactosidase.

30. The method of claim 25, wherein the contacting step (a) further comprises exposing the support to a ligand complementary to the sbp member, said ligand being linked to a label, whereby said autoantibody and ligand compete for binding to the sbp member on the support, and the detecting step (b) comprises detecting the label bound to the support, wherein the amount of label bound to the support is correlated to the presence of the autoantibody.

31. The method of claim 30, wherein the label is an enzyme.

32. The method of claim 31, wherein the enzyme is horseradish peroxidase, alkaline phosphatase or β-galactosidase.

33. A composition comprising an autoantibody which binds to tryptase and tryptase.

34. The composition of claim 33, said composition being attached to a solid support.

35. A method of forming an immune complex of a tryptase autoantibody and tryptase, wherein said complex is bound to a solid support, said method comprising:
   (a) providing a solid support comprising tryptase immobilized therein;
   (b) exposing the solid support to a sample containing the autoantibody, whereby the autoantibody binds to the tryptase to form said immune complex; and
   (c) isolating the solid support, to provide the immune complex bound to the solid support.

* * * * *